US006821526B1

(12) United States Patent
Huang

(10) Patent No.: US 6,821,526 B1
(45) Date of Patent: Nov. 23, 2004

(54) COMPOSITIONS AND DEVICES USING A SPINOSYN COMPOUND FOR CONTROL OF INSECTS

(75) Inventor: Xinpei Huang, Greenville, MS (US)

(73) Assignee: Dow Agrosciences, LLC, Indianapolis, IN (US)

( * ) Notice: Subject to any disclaimer, the term of this patent is extended or adjusted under 35 U.S.C. 154(b) by 0 days.

(21) Appl. No.: 10/424,048

(22) Filed: Apr. 25, 2003

Related U.S. Application Data

(62) Division of application No. 09/799,219, filed on Mar. 5, 2001, now Pat. No. 6,585,990.

(51) Int. Cl.$^7$ .............................................. A01N 25/02
(52) U.S. Cl. ........................ 424/410; 424/84; 424/405; 424/406; 514/28; 514/31; 43/122; 43/131
(58) Field of Search ................................ 43/122, 132.1, 43/131, 133; 514/28–31; 424/405, 406, 407, 409, 403, 410, 414

(56) References Cited

U.S. PATENT DOCUMENTS

| | | | |
|---|---|---|---|
| 1,916,982 A | | 7/1933 | Jones |
| 4,310,985 A | | 1/1982 | Foster et al. |
| 4,351,834 A | | 9/1982 | Takahashi et al. |
| 4,638,592 A | * | 1/1987 | Schneidmiller .............. 43/122 |
| 4,886,899 A | | 12/1989 | Jacobs |
| 4,908,977 A | | 3/1990 | Foster |
| 5,202,242 A | | 4/1993 | Mynderse et al. |
| 5,359,808 A | * | 11/1994 | Fitsakis ..................... 43/132.1 |
| 5,362,634 A | | 11/1994 | Boeck et al. |
| 5,496,931 A | | 3/1996 | Boeck et al. |
| 5,501,033 A | | 3/1996 | Wefler et al. |
| 5,567,429 A | | 10/1996 | Senbo |
| 5,571,901 A | | 11/1996 | Boeck et al. |
| 5,591,606 A | | 1/1997 | Turner et al. |
| 5,631,155 A | | 5/1997 | Turner et al. |
| 5,670,364 A | | 9/1997 | Mynderse et al. |
| 5,670,486 A | | 9/1997 | Mynderse et al. |
| 5,767,253 A | | 6/1998 | Turner et al. |
| 5,840,861 A | | 11/1998 | Mynderse et al. |
| 5,972,330 A | | 10/1999 | Sugiura et al. |
| 6,063,771 A | * | 5/2000 | Snyder ........................ 514/31 |
| 6,455,504 B1 | * | 9/2002 | Lewer et al. ................. 514/31 |

FOREIGN PATENT DOCUMENTS

| | | | |
|---|---|---|---|
| EP | 0378431 | * | 7/1990 |
| WO | WO 9309126 A1 | | 5/1993 |
| WO | WO 9420518 | | 9/1994 |

OTHER PUBLICATIONS

Adan, A. et al. "Laboratory Evaluation of the Novel Naturally Derived Compound Spinosad against *Ceratitis capitata*" *Pestic. Sci.*, 1996, pp. 261–268, vol. 48.

Box, G.E.P. et al. *Statistics for Experimenters: An Introduction to Design, Data Analysis, and Model Building*, 1978, pp. 204–205 and 222–223, John Wiley & Sons, New York.

King, J. R. et al. "Spinosad Bait for the Caribbean Fruit Fly (Diptera: Tephritidae)" *Florida Entomologist*, 1996, pp. 526–531, vol. 79, No. 4.

Kirst, H.A. et al. "A83543A–D, Unique Fermentation–Derived Tetracyclic Macrolides" *Tetrahedron Letters* 1991, 4839–4842, vol. 32, No. 37.

Metcalf, R.L. et al. "Insects that Affect the Health of Humans" In: *Destructive and useful Insects: their habits and control*, 1993, pp. 21.42–21.47, McGraw–Hill, Inc., Frank J. Kotowski, Jr., ed.

Scott, J. G. "Toxicity of Spinosad to Susceptible and Resistant Strains of House Flies, *Muscle domestica*" *Pestic. Sci.*, 1998, pp. 131–133, vol. 54.

"New Products Presented at the CIRA Conference" *Phytoma. La Defense Des Vegeteaux*, 1999, pp. 38–40, vol. 522.

\* cited by examiner

Primary Examiner—Neil S. Levy
(74) Attorney, Agent, or Firm—Saliwanchik, Lloyd & Saliwanchik

(57) ABSTRACT

The subject invention pertains to compositions and devices for controlling insects and, in particular, houseflies. Insecticidal compositions of the present invention comprise spinosad and, optionally, insect foodstuffs and attractants. The devices of the invention are directed to a housefly bait device that includes an insecticidal composition of the present invention. The invention also concerns methods for controlling insects, such as houseflies, using the present compositions and devices.

23 Claims, 4 Drawing Sheets

COMPOSITIONS AND DEVICES USING A SPINOSYN COMPOUND FOR CONTROL OF INSECTS

CROSS-REFERENCE TO RELATED APPLICATION

This application is a divisional of U.S. application Ser. No. 09/799,219, filed Mar. 5, 2001, now U.S. Pat. No. 6,585,990.

BACKGROUND OF THE INVENTION

The common housefly, *Musca domestica*, is present at one time or another in nearly every habitation in the world. Exposure to manure piles, sewage, garbage, sputum, animal carcasses, food of all kinds, and to the lips, eyes, and nursing bottles of sleeping children is "all in the day's work" for a housefly. In addition to its disagreeable presence and habits, the housefly has long been suspected as a vector of many human and animal diseases. For example, in India and North Africa the housefly is a major factor in the spread of the *trachoma* virus and its associated *Haemophilus* bacterium that afflicts 80 million people and is a major cause of blindness (Metcalf and Metcalf, 1993). If uncontrolled, houseflies in Europe compromise animal production and the housefly control market in this area alone is $10–20 MM. Residual spraying with organochlorine, organophosphorus, carbamate, and pyrethroid insecticides on residential or animal-rearing structures has increasingly been of public concern and rapidly results in the selection of cross-resistant fly strains.

A safe, fast-acting, and resistance-reducing or preventing housefly control method is needed. Denmark and the United Kingdom have been pursuing various control mechanisms combined with baiting strategies as the primary means of controlling houseflies for livestock producers. A formulation containing a sugar base, an attractant, and a non-repellant toxicant has been a bait standard.

The fermentation product identified in U.S. Pat. No. 5,362,634 as A83543 is a family of related compounds produced by *Saccharopolyspora spinosa*. These compounds have been referred to as factors or components A, B, C, D, E, F, G, H, J, K, L, M, N, O, P, Q, R, S, T, U, V, W, Y, and the like (also see published international patent application WO 93/09126 and WO 94/20518) and are hereinafter referred to as spinosyn A, B, C, and so on. Spinosyn compounds are environmentally friendly and have an appealing toxicological profile. The naturally produced spinosyn compounds consist of a 5,6,5-tricylic ring system, fused to a 12-membered macrocyclic lactone, a neutral sugar (rhamnose), and an amino sugar (forosamine) (see Kirst et al. (1991)). Natural spinosyn compounds may be produced via fermentation from cultures deposited as NRRL 18719, 18537, 18538, 18539, 18743, 18395, and 18823 of the stock culture collection of the Midwest Area Northern Regional Research Center, Agricultural Research Service, United States Department of Agriculture, 1815 North University Street, Peoria, Ill. 61604. Spinosyn compounds are also disclosed in U.S. Pat. Nos. 5,496,931, 5,670,364, 5,591,606, 5,571,901, 5,202,242, 5,767,253, 5,840,861, 5,670,486, and 5,631,155. The spinosyn compounds are useful for the control of arachnids, nematodes, and insects, in particular Lepidoptera and Diptera species.

Spinosyn A and spinosyn D are two spinosyns that are particularly active insecticides. A product comprised mainly of these two spinosyns (approximately 85% spinosyn A and approximately 15% spinosyn D) is produced by Dow AgroSciences (Indianapolis, Ind.) known as spinosad. Spinosad is an active ingredient of several insecticidal formulations available commercially from Dow AgroSciences, including the TRACER, SUCCESS, SPINTOR, and CONSERVE insect control products. For example, the TRACER product is comprised of about 44% to about 48% spinosad (w/v), or about 4 pounds of spinosad per gallon.

It has been reported that spinosad is highly toxic to houseflies under experimental conditions in which spinosad was applied to the thoracic notum of the flies (Scott, 1998). King and Hennessey (1996) described the use of an insecticidal composition comprising spinosad in a sugar and yeast hydrolysate mixture to control Caribbean fruit flies. Adán et al. (1996) disclosed that adult *C. capitata* were susceptible to spinosad through residual contact with spinosad dried on glass plates and via ingestion in drinking water.

Typically, a bait station device is employed to deliver an insecticide for the control of insects in a household or commercial environment when minimal exposure to persons or other animals is desired. A number of bait station devices containing insecticide have been described in the art. For example, U.S. Pat. No. 5,501,033 discloses a two-stage liquid bait-toxicant delivery device having an upper and lower reservoir which allows for sequential delivery of two separate liquids to an absorbent feeding pad, e.g., delivery of a bait-only formulation first, followed by a bait-toxicant formulation once the bait-only formulation is expended. Liquid is delivered from the lower reservoir to the absorbent pad via a wicking system. The device is designed to "train" flying insects such as wasps to feed at the device using the bait-only formulation before they are exposed to the bait-toxicant formulation.

U.S. Pat. No. 4,310,985 (the '985 patent) discloses a device for killing arthropods that uses an absorbent material onto which an insecticide is applied and allowed to dry. When the device is ready to be used, one portion of the insecticide-coated absorbent material and/or a wicking material is placed into a solution such as water. Arthropods contacting the moistened absorbent material are killed by the insecticide.

U.S. Pat. No. 4,908,977 discloses a device similar to that in the '985 patent mentioned above. The device, which can be used in a "wet" or "dry" form, comprises a target area containing an insecticide. In the wet form, fluid in a reservoir is wicked to the target area so that the target area remains moist while in use.

U.S. Pat. No. 1,916,982 discloses a device that uses an absorbent pad impregnated with a fly poison. One portion of the pad is in contact with a water-filled reservoir to maintain moisture throughout the pad. The moistened pad draws from an adjacent cavity containing a sugar and fly poison mixture.

Various insecticidal baits and attractants have also been described in the art. For example, U.S. Pat. No. 4,351,834 discloses an insecticidal bait for the control of houseflies that comprises an insecticide plus sugar and milk mixed in sugar water and absorbed onto absorbent cotton material. Houseflies were allowed to feed on the material to determine the activity of the composition.

U.S. Pat. No. 4,886,899 (the '899 patent) discloses housefly chemosterilants provided in a fly feed mixture comprising, for example, dried milk, sugar, powdered eggs, malt, molasses, and yeast. The '899 patent also discloses drying a solution of the chemosterilant/feed mixture to prepare a dry feed which is made available to the flies in a bait dispenser.

U.S. Pat. No. 5,567,429 discloses pest controlling compositions that include bait and attracting substances including flour, corn powder, starches, sugars, glycerin, and food flavors such as milk flavor.

U.S. Pat. No. 5,972,330 discloses pesticidal baits that comprise insect attractants and baiting substances such as cereal powders, starches, and sugars.

As can be seen from the above, there have been numerous efforts to control flying insects, however, many of these use insecticides that do not have a particularly appealing toxicological profile or have not been particularly effective. Thus, there remains a need in the art for simple but effective bait devices for controlling houseflies. An effective bait device should use a long lasting and cost-efficient attractant to attract flies to the bait. The insecticide incorporated in the bait device should be one that can be used at a very low concentration in the bait in order to obtain an efficacy which is equivalent or superior to current commercial bait standards. The present invention advantageously provides a housefly bait station which is safe, highly effective, stable during storage, and transportation, affordable to customers, and easy to use (users need to add only water to the station before use). It has been discovered that incorporating spinosad as the insecticide, in conjunction with a volatile fly attractant and feeding stimulant has numerous advantages over conventional broadcast applications of granular baits for housefly control. The bait station devices of the present invention greatly reduce the amount of active ingredient used and exert less impact on non-target organisms.

BRIEF SUMMARY OF THE INVENTION

The subject invention concerns compositions and devices for controlling houseflies. The compositions of the present invention comprise the insecticide spinosad. The devices of the invention are directed to a housefly bait device that includes a means for providing bait materials comprising a housefly attractant, a feeding stimulant, and spinosad in an environment where control of houseflies is required. The device is inexpensive to construct, convenient to transport and store, easy, and safe to apply and clean up, and is highly effective in the control of houseflies. In a preferred embodiment, the device of the invention uses "bars" that are prepared by coating bait materials onto a portion of an absorbent material. In an exemplified embodiment, the absorbent material is a cotton roll.

In one embodiment, a commercially available spinosad formulation is used as the insecticide. In an alternative embodiment, a spray dried waste broth containing spinosad resulting from spinosad production is used as the toxin. When used to control houseflies, however, the spinosad formulation can be wetted to significantly increase its attractiveness and knockdown power. In one embodiment, the spinosad used in the formulation is obtained from the TRACER insect control product.

A bait material bar of the present invention containing adult fly food, yeast, cornmeal, and 0.1% spinosad (dry weight) provided more effective control of houseflies than did a commercial standard (1% methomyl) within eight (8) hours. The subject bar continued to outperform the standard at 24 and 32 hours after exposure.

DETAILED DISCLOSURE OF THE INVENTION

The subject invention concerns compositions and devices for controlling insects and, in particular, houseflies. Insecticidal compositions of the present invention preferably comprise spinosad and, optionally, insect foodstuffs and attractants. As used herein, the term "spinosad" refers to a composition comprising a combination of spinosyn A and spinosyn D. The devices of the invention are directed to a housefly bait device that includes an insecticidal composition of the present invention.

One embodiment of an insecticidal composition of the present invention comprises the following: spinosad; one or more foodstuffs that insects will feed on; and one or more insect attractants. In a preferred embodiment, for the control of houseflies, the foodstuff can include one or more of the following foods: sugar, milk, and eggs. The attractant can include one or more of the following ingredients: cornmeal and yeast. The foodstuff can make up to about 60% of the insecticidal composition (dry weight). In one embodiment, the insecticidal composition can optionally contain from about 30% to about 40% of cornmeal (dry weight). In another embodiment, the insecticidal composition can optionally contain, in addition to or apart from cornmeal, from about 2% to about 4% of yeast (dry weight).

Preferably, the spinosad used in the insecticidal composition comprises about 85% spinosyn A and about 15% spinosyn D. In a preferred embodiment, the insecticidal composition comprises from about 0.01% to about 1% spinosad (dry weight). Preferably, the insecticidal composition comprises about 0.1% spinosad (dry weight). The present invention also contemplates for the insecticidal composition the use of spinosyn A in the absence of spinosyn D and the use of spinosyn D in the absence of spinosyn A.

In one embodiment, spinosad is provided in the form of a waste broth. The spinosyn waste broth can be obtained as a consequence of a fermentation run to produce spinosad and when used should contain sufficient spinosad to be insecticidal. Preferably, the waste broth comprises about 0.028% spinosad (dry weight). Preferably, the insecticidal composition comprises about 60% spinosad waste broth (dry weight).

In a further embodiment, the insecticidal composition can be prepared with water. Preferably, the insecticidal composition is prepared as a slurry in a ratio of about one gram of dry material to about one milliliter of water. More preferably, the insecticidal composition is prepared as a slurry in a ratio of about one gram of dry material to about 0.5 milliliter of water.

Figure 1A:
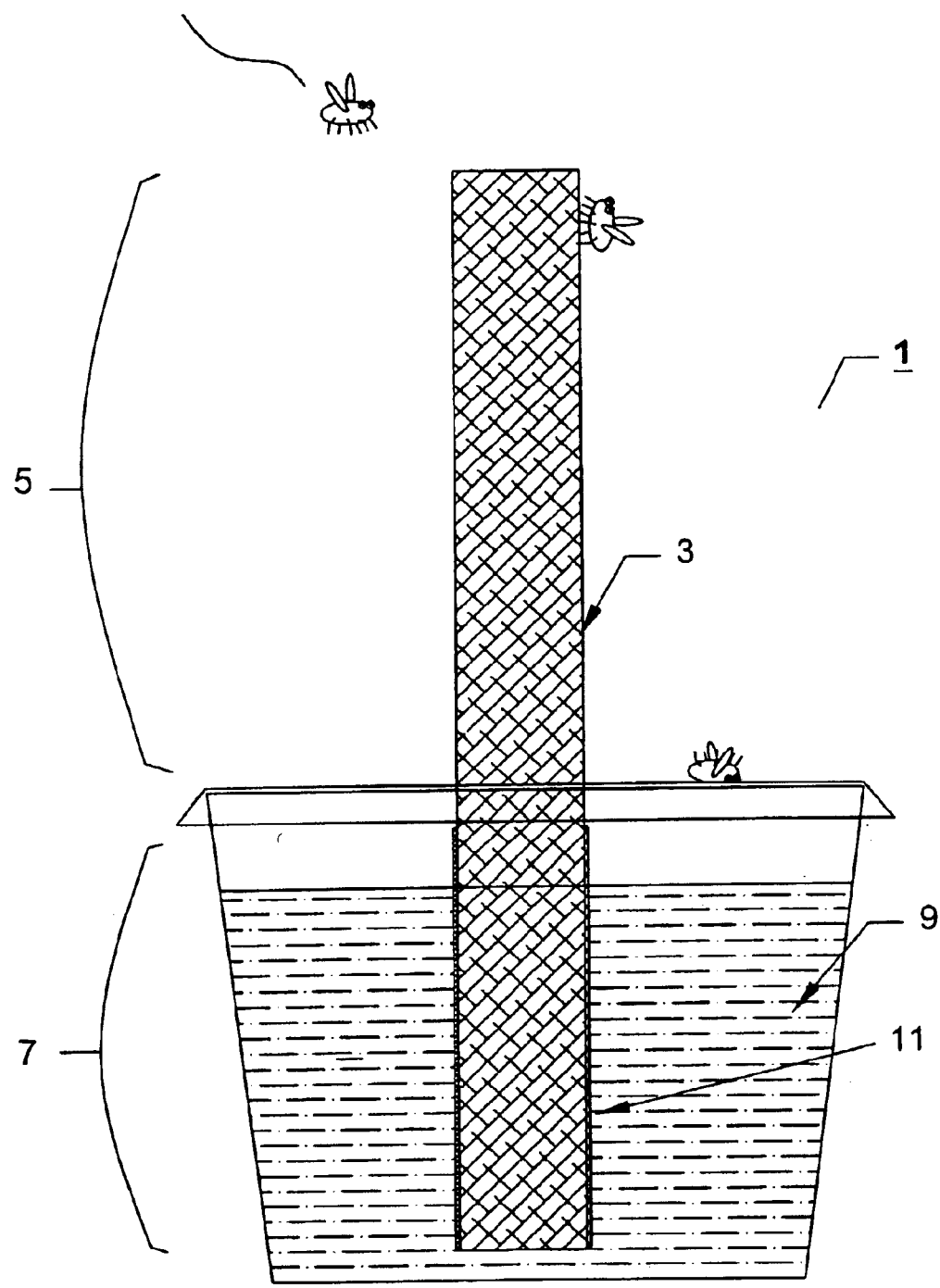
FIG. 1A shows a cross-sectional representation of a device according to the present invention.

The subject invention also concerns a bait station device to provide insecticidal compositions of the present invention for controlling insects, such as houseflies. As can be understood from reference to FIGS. 1A–1C, the bait station device 1 comprises an absorbent material 3 having an upper portion 5 and a lower portion 7, and a reservoir 9 capable of containing a solution and adapted for releasably holding the lower portion of the absorbent material in the solution. In one embodiment, the lower portion of the absorbent material is substantially covered by or wrapped in a non-absorbent material 11, such as plastic and the like. The terminal end of the lower portion of the absorbent material is not covered by the non-absorbent material and thereby allows that portion of the absorbent material to directly contact the solution. The upper portion of the absorbent material is absorbed with an insecticidal composition of the invention.

The absorbent material can be composed of any suitable material that is capable of absorbing a fluid and moving the fluid from one end of the material to the other by a wicking action when the lower portion is brought into contact with a solution, such as water. Absorbent materials contemplated for use with the invention include, for example, cotton, absorbent papers, sponge (both natural and synthetic), and the like.

In an exemplified embodiment, a device of the invention uses "bars" that are prepared by coating bait materials onto a portion of the absorbent material. Bait material bars were constructed by coating a mixture of an insecticidal composition of the invention onto a portion of 6-inch cotton rolls (approximately ⅜-inch in diameter). The coated cotton rolls were then air-dried and stored at room temperature until use. When in use, the non-coated section of a bait material bar was immersed in water in the reservoir of the bait station device. Different bait materials were tested, and the most effective combination was found to be superior to a commercial standard bait, Improved GOLDEN MALRIN bait, under several test conditions.

The devices of the present invention can contain a means for attracting insects and/or a means of inducing a feeding response of the insects. Preferably, the means for attracting and/or inducing a feeding response is specific for houseflies. One means for attracting flies comprises the use of a pheromone, such as cis-9-tricosene, on the subject device or in the compositions used with the device. The devices of the invention can also include antimicrobial agents, for example, an antifungal agent to control the growth of mold on a wetted bait material bar. The skilled artisan can readily select antimicrobial agents that are specific for controlling unwanted microbial growth but that will not prevent yeast fermentation during use of a bait material that comprises yeast.

Bait devices of the present invention are inexpensive to construct, convenient to transport and store, easy and safe to apply and clean up, and highly effective, The devices have a compact structure and can remain dry for storage and handling convenience. When used to control houseflies, a subject device can be easily wetted to significantly increase its attractiveness and knockdown power. Bait bars of the invention containing adult fly food, yeast, cornmeal, and 0.1% spinosad provided more effective control of houseflies than the Improved GOLDEN MALRIN bait standard within eight (8) hours. This embodiment continued to outperform the standard at 24 and 32 hours after exposure. Because spinosad has a favorable toxicological profile, the compositions and bait devices of the present invention possess the potential for residential as well as industrial use.

The subject invention also concerns methods for controlling insects, such as houseflies, using the present compositions and devices. Methods of the invention comprise providing an insecticidal composition in a bait station device of the present invention.

All patents, patent applications, provisional applications, and publications referred to or cited herein are incorporated by reference in their entirety to the extent they are not inconsistent with the explicit teachings of this specification.

Materials and Methods

Insects and Chemicals. Housefly (*Musca domestica*) pupae were purchased from Carolina Biological Supply Co., or provided by Dow AgroSciences Insectary of Indianapolis, Ind. Pupae were kept in metal screen cages under room temperature until emergence. Emerged flies were supplied with adult fly food and water for 2–4 days before being used. Yeast was purchased from Sigma Chemical Co. Adult fly food comprised 4 parts powdered sugar/4 parts powdered milk/2 parts powdered eggs and was obtained from the Dow AgroSciences Insectary. Improved GOLDEN MALRIN bait (1% methomyl, 0.025% Z-9-tricosene, and sugar) and cornmeal were purchased from local stores.

Bait material Bars. In addition to a commercially available spinosad formulation, a spray dried spinosad waste broth was also used as a toxin as well as a bait substance. The waste broth consisted of 0.028% spinosad and approximately 50% sugar. Five different combinations of coating materials were tested:

test combination A—25% adult food+75% spinosad waste broth (dry weight)

test combination B—99.99% adult food+0.01% spinosad (dry weight)

test combination C—99.9% adult food+0.1% spinosad (dry weight)

test combination D—59.9% adult food+37% corn+3% yeast+0.1% spinosad (dry weight)

test combination E—20% adult food+17% corn+3% yeast+60% spinosad waste broth (dry weight)

Figures 1B, 1C:
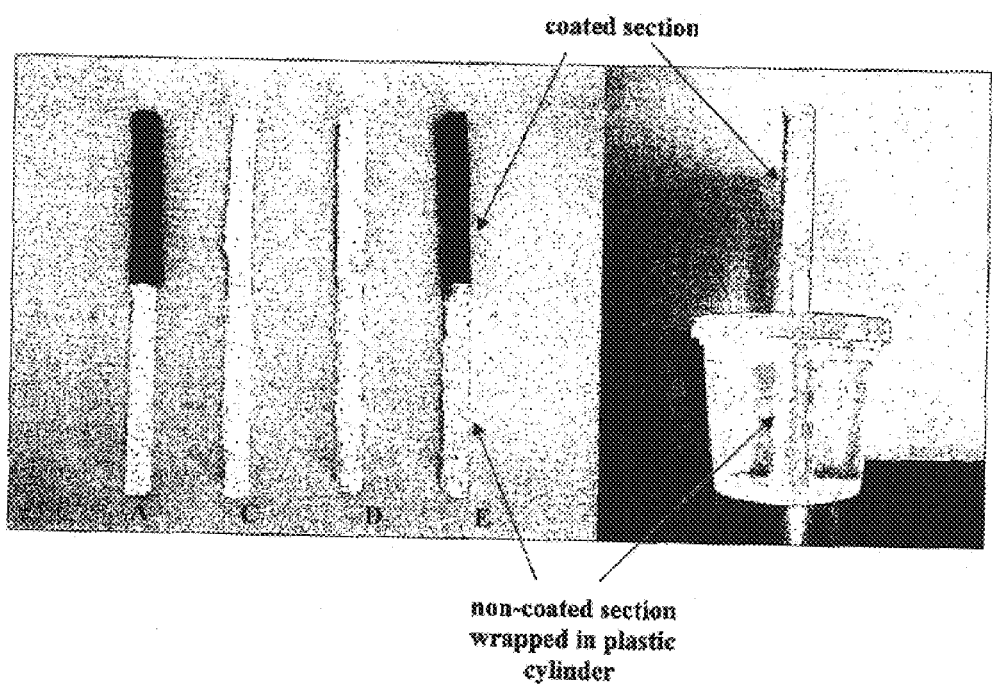
FIG. 1B shows bait material bars used in a device of the present invention prepared by coating housefly bait compositions onto cotton rolls, with the non-coated section wrapped in transparent plastic material.
FIG. 1C shows a device of the present invention wherein the non-coated section of a bar is in contact with a solution for wetting the section of the bar coated with bait material.

To coat the bait materials onto cotton rolls, water was added to the above mixtures of dry material to make a slurry at a ratio (g dry material: ml $H_2O$) of 1:1 (for preparations A and E) or 1:0.5 (for preparations B, C, and D). The non-coated section (3 inches long) of the cotton roll was tightly wrapped in a thin plastic cylinder with both ends opened (FIG. 1B). The plastic cylinder was used to slow down the movement of bait materials from the coated section to the non-coated section and to help keep the bait material "bars" in an erect position when in use. The coated bait material bars were air-dried with an electric fan for six (6) to eight (8) hours and stored at room temperature until use. The total dry weight of bait materials coated onto each bar ranged from 1.5 g to 2.3 g.

Bioassay Setup. Assays were conducted in 24"×24"×24" or 18"×18"×18" metal screen cages under laboratory conditions. Seventy to 150 flies were introduced into each cage on the day before assays and were supplied with adult fly food and water. To start the tests, a 4 ounce plastic cup was filled with water, and the wrapped non-coated section of a bait material bar was inserted into the cup through a hole made in the center of the cap (FIG. 1C). The cup with bar was then presented to flies in a cage. The commercial standard, Improved GOLDEN MALRIN bait (2 g), was presented to flies in a weigh boat. In non-choice tests (Example 1), the food and water supplies were removed from cages prior to test, and flies were exposed to a bait material bar or the standard alone. In choice tests (Examples 2, 3, and 4), adult fly food and water were supplied to the flies, in addition to either the bar or the commercial standard. Efficacy of the bars and commercial standard was evaluated by calculating the accumulative percent mortality and knockdown of the houseflies at 4, 8, 24, and 32 hours. Tests were replicated 2–3 times.

Following are examples which illustrate procedures for practicing the invention. These examples should not be construed as limiting. All percentages are by weight and all solvent mixture proportions are by volume unless otherwise noted.

EXAMPLE 1

Figure 2:
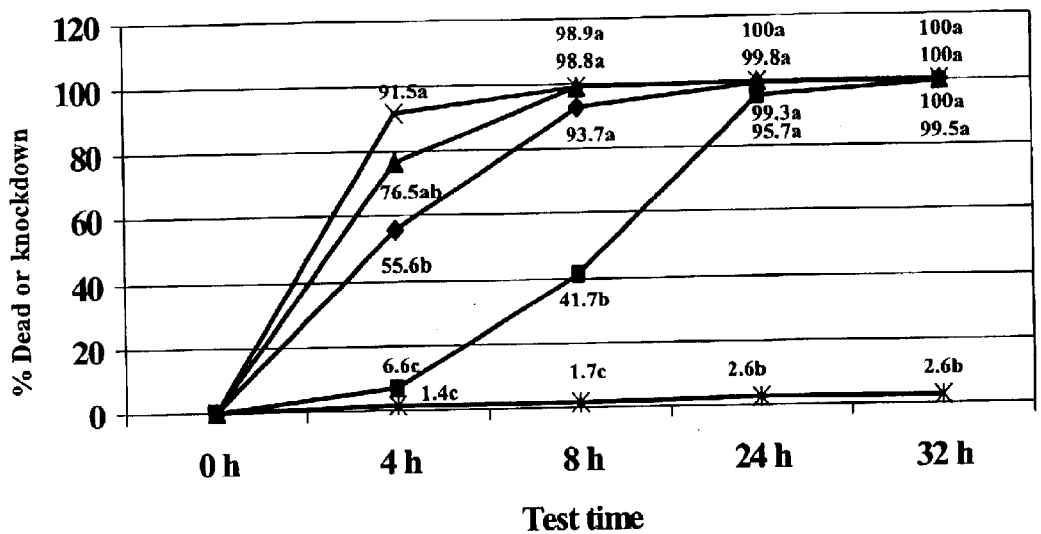
FIG. 2 shows the efficacy of a device of the present invention against the housefly, *Musca domestica*, in non-choice (no alternative food and water supply) tests. The non-coated portion of bars are immersed in water, starting one hour before the test. Tukey's "Honestly Significant Difference" (HSD) procedure (Box et al., 1978), which tests the pairwise comparisons among means, was used on each time point, $p \leq 0.10$. In the graph, ◆ represents food+spinosad waste broth; ■ represents food+0.01% spinosad; ▼ represents food+0.1% spinosad; X represents Improved GOLDEN MALRIN bait; and ✖ represents untreated control. The lower case letters, "a", "b", and "c" are identifiers which indicate whether or not the difference between a given value (mean) within a time point is statistically different from another given value within the same time point. Two values sharing a common letter within their identifiers are not significantly different from each other, according to the Tukey's HSD test.

Preliminary non-choice testing was used to explore the possibility of using cotton rolls coated with bait materials for control of houseflies. Bait material bars coated with adult fly food and spinosad waste broth (test combination A) or adult fly food and spinosad (test combinations B and C), or the standard Improved GOLDEN MALRIN bait were exposed to flies in individual cages without alternative food or water sources in the cage. As shown in FIG. 2, test combination C with 0.1% spinosad (dry weight) provided much more effective control (76.5%) of flies at four hours after exposure (4HAE) than did test combination B with 0.01% spinosad (6.6% control). There was no significant difference between test combination B and the non-insecticide treatment (untreated) at this time. Test combination A, which consisted of 75% spinosad waste broth and 25% adult fly food (dry weight), also caused 55.6% dead or knockdown. The highest percent dead or knockdown was obtained with the commercial standard at 4HAE, as shown in FIG. 2. At 8HAE 98.8% control was obtained using test combination C, equivalent to the control obtained with the standard. As compared with 4HAE, much higher percent mortality and knockdown was detected in cages equipped with test combination A (93.7%) or B (41.7%) at 8HAE. There were no survival of flies exposed to test combination C at 24HAE. As shown in FIG. 2, higher than 95% control were obtained with test combination A or B at 24HAE. These results indicate that bait material bars of the present invention were effective for control of houseflies. The data also suggested that the use of at least 0.1% spinosad (dry weight) was necessary to obtain acceptable speed of kill. As used herein, the terms "kill" and "control" refer to both death (i.e., mortality) and knockdown (i.e., partial or complete paralysis from which the fly does not recover).

Under situations where no alternative food and water sources were available to flies, it is possible to gain effective control of flies within eight (8) hours using test combinations A, B, and C in the present devices. In places where houseflies usually live, however, alternative food and water supplies may be available to them. Therefore, a bait must be more attractive than alternatives in order that the flies come to and feed on the bait. With this in mind, yeast and cornmeal were incorporated into the coating mixtures. In a preliminary behavioral experiment where bait material bars with yeast/cornmeal were compared to bait material bars without yeast/cornmeal in the same cage, bars containing the yeast/cornmeal mix were more attractive to flies (data not presented here). Therefore, only compositions comprising a yeast/cornmeal mix were examined in the following tests.

EXAMPLE 2

Figure 3:
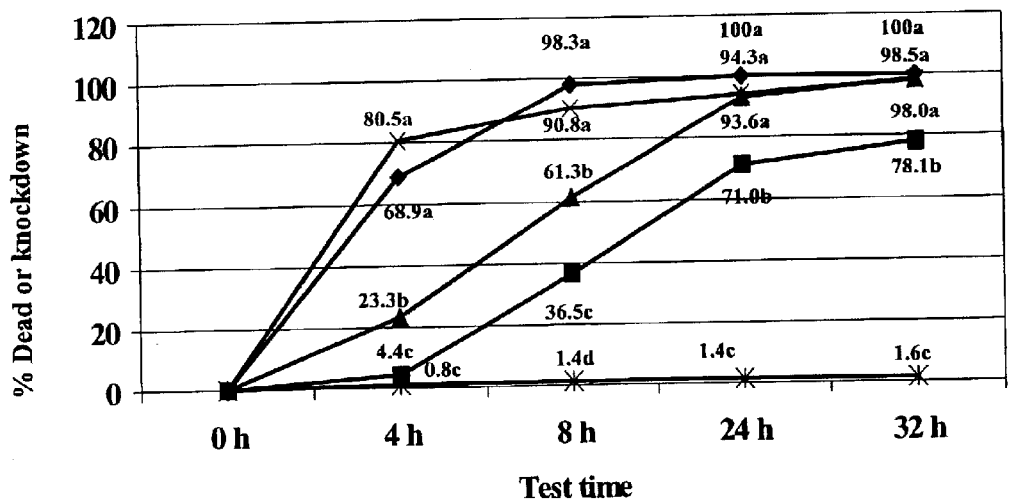
FIG. 3 shows the efficacy of a device of the present invention against the housefly, *Musca domestica*, in choice (with alternative food and water supply) tests. The non-coated portion of bars are either immersed (starting one hour before test) or not immersed in water. Tukey's HSD on each time point, $p \leq 0.10$. In the graph, ◆ represents food+cornmeal+yeast+0.1% spinosad (immersed); ■ represents food+cornmeal+yeast+0.1% spinosad (not immersed); ▼ represents food+cornmeal+yeast+spinosad waste broth; X represents Improved GOLDEN MALRIN bait; and ✖ represents untreated control. The lower case letters, "a", "b", and "c" are identifiers which indicate whether or not the difference between a given value (mean) within a time point is statistically different from another given value within the same time point. Two values sharing a common letter within their identifiers are not significantly different from each other, according to the Tukey's HSD test.

Test combinations D and E were evaluated in this choice test against the standard Improved GOLDEN MALRIN bait. In addition to test combinations D or E, or Improved GOLDEN MALRIN bait, adult fly food, and water were supplied to flies in the same cage. To further confirm the importance of moisture in the effectiveness of the bait material bars, for comparison, test combination D was presented to flies with the non-coated section of the bar not immersed in water. Test combination E and the immersed test combination D were placed in water one hour before tests. FIG. 3 demonstrates relative efficacy of test combination D ("dry" vs. "wetted"), test combination E, and Improved GOLDEN MALRIN bait. The bait material bar which contained test combination D and which was exposed to water provided 68.9% control of flies at 4HAE, significantly higher than a bait material bar that contained test combination D but that was not exposed to water. The test combination E containing spinosad waste broth provided 23.3% control and was inferior to test combination D, as shown in FIG. 3, which was probably due to lower concentration of the active ingredient and/or less favorable smell from the broth. The percent mortality or knockdown caused by the water-exposed test combination D was numerically lower than that achieved by the standard at this time. At 8HAE, however, the immersed test combination D provided the highest percent control (98.3%) among the baits including Improved GOLDEN MALRIN bait. Only 90.8% mortality or knockdown was obtained using Improved GOLDEN MALRIN bait. Although there was a significant difference between the bar containing "dry" test combination D and the untreated bar at 8HAE, efficacy of the bar with the "dry" test combination D was significantly lower than the "wetted" test combination D containing bait material bar. While all flies baited with "wetted" test combination D were dead or knocked down at 24HAE, 5.7% of the flies in cages baited with the standard were still alive, as shown in FIG. 3. Test combination E provided a similar control of flies as compared with the Improved GOLDEN MALRIN bait standard at 24HAE. None of the treatments, except "wetted" test combination D, provided 100% control of flies at 32HAE in this choice test.

The water in the cup accommodating bait material bars became slightly cloudy after two days following immersion, indicating some of the active spinosad might have moved from the coated section to the non-coated section and to the water. Furthermore, some green mold developed on the baited area after the non-coated section of a bar had been immersed in water for about five (5) days. The experiments reported in Examples 3 and 4 below were therefore conducted to reevaluate the residual efficacy of aged water-immersed bars.

EXAMPLE 3

Figure 4:
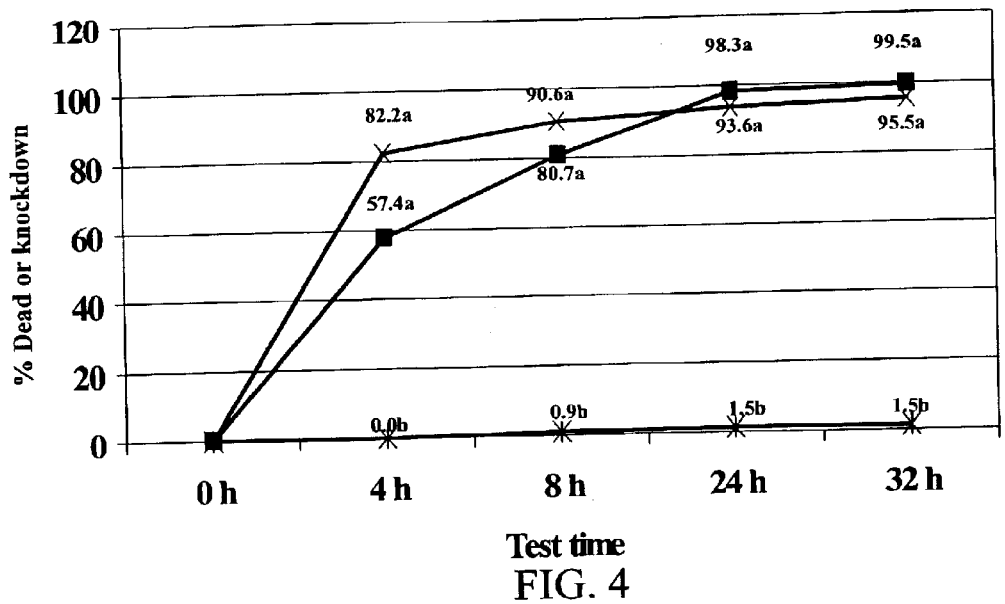
FIG. 4 shows the efficacy of a device of the present invention against the housefly, *Musca domestica*, in choice (with alternative food and water supply) tests. The non-coated portion of bars are immersed in water for three (3) days before the test. Tukey's HSD on each time point, $p \leq 0.10$. In the graph, ■ represents food+cornmeal+yeast+0.1% spinosad; X represents Improved GOLDEN MALRIN bait; and ✖ represents untreated control. The lower case letters, "a", "b", and "c" are identifiers which indicate whether or not the difference between a given value (mean) within a time point is statistically different from another given value within the same time point. Two values sharing a common letter within their identifiers are not significantly different from each other, according to the Tukey's HSD test.

Only test combination D was compared with the standard Improved GOLDEN MALRIN bait in this choice test where alternative adult fly food and water supplies were available to flies. The non-coated section of test combination D had been immersed in water for three days before the test. As shown in FIG. 4, test combination D provided 57.4% control at 4HAE, as compared to 82.2% control by the standard. The difference between test combination D and the standard became smaller at 8HAE. However, not until 24HAE did test combination D outperform Improved GOLDEN MALRIN bait, with 98.3% control by test combination D and 93.6% control by the standard. As shown in FIG. 4, a control of 99.5% was obtained for test combination D at 32HAE that continued to be numerically higher than the control provided by the standard.

EXAMPLE 4

Figure 5:
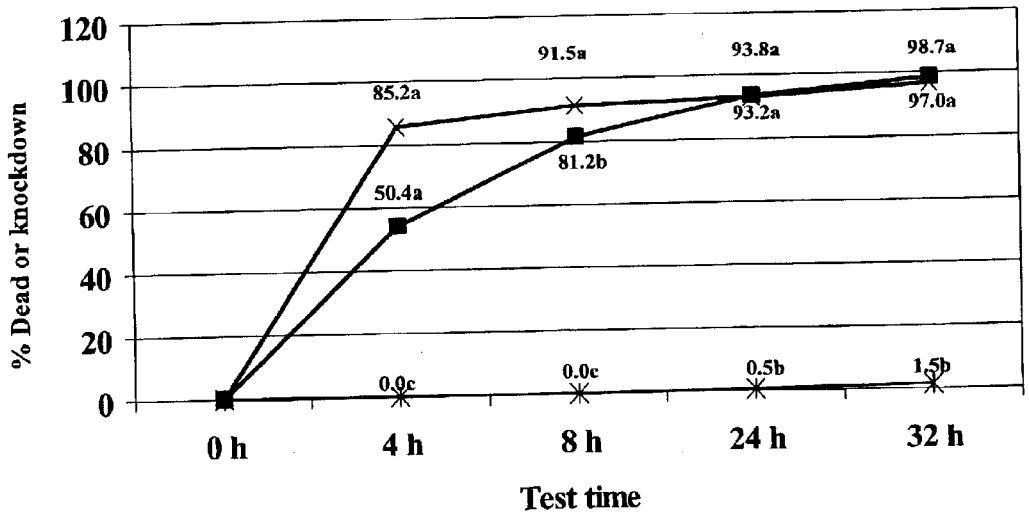
FIG. 5 shows the efficacy of a device of the present invention against the housefly, *Musca domestica*, in choice (with alternative food and water supply) tests. The non-coated portion of bars are immersed in water for seven (7) days before the test. Tukey's HSD on each time point, $p \leq 0.10$. In the graph, ■ represents food+cornmeal+yeast+0.1% spinosad; X represents Improved GOLDEN MALRIN bait; and ✖ represents untreated control. The lower case letters, "a", "b", and "c" are identifiers which indicate whether or not the difference between a given value (mean) within a time point is statistically different from another given value within the same time point. Two values sharing a common letter within their identifiers are not significantly different from each other, according to the Tukey's HSD test.

This test used the same design as Example 3, except that the non-coated section of test combination D had been immersed in water for seven days before testing. The efficacy of a 7-day immersion test combination D (FIG. 5) continued to decline slightly as compared with a 3-day immersion test combination D (FIG. 4). Test combination D provided 50.4% control at 4HAE, significantly lower than that provided by the standard (FIG. 5). Test combination D did catch up, though, and the same control was obtained with test combination D as with the standard by 24HAE. The advantage of test combination D over the Improved GOLDEN MALRIN bait standard was less obvious at the end of this assay than those observed in Examples 2 and 3.

It should be understood that the examples and embodiments described herein are for illustrative purposes only and that various modifications or changes in light thereof will be suggested to persons skilled in the art and are to be included within the spirit and purview of this application and the scope of the appended claims.

References

U.S. Pat. No. 5,362,634
U.S. Pat. No. 5,496,931
U.S. Pat. No. 5,670,364
U.S. Pat. No. 5,591,606
U.S. Pat. No. 5,571,901
U.S. Pat. No. 5,202,242
U.S. Pat. No. 5,767,253
U.S. Pat. No. 5,840,861
U.S. Pat. No. 5,670,486
U.S. Pat. No. 5,631,155
U.S. Pat. No. 5,501,033
U.S. Pat. No. 4,310,985
U.S. Pat. No. 4,908,977
U.S. Pat. No. 1,916,982
U.S. Pat. No. 4,351,834
U.S. Pat. No. 4,886,899
U.S. Pat. No. 5,567,429
U.S. Pat. No. 5,972,330
WO 93/09126
WO 94/20518
Adán, Angeles et al. (1996) "Laboratory Evaluation of the Novel Naturally Derived Compound Spinosad against *Ceratitis capitata*" *Pestic. Sci* 48:261–268.
Box, G. E. P. et al. (1978) *Statistics for Experimenters: An Introduction to Design, Data Analysis, and Model Building*, John Wiley & Sons, New York, pages 204–205 and 222–223.
King, Jimmie R. et al. (1996) "Spinosad Bait for the Caribbean Fruit Fly (Diptera: Tephritidae)" *Florida Entomologist* 79(4):526–531.
Kirst, H. A. et al. (1991) "A83543A-D, Unique Fermentation-Derived Tetracyclic Macrolides" *Tetrahedron Letters* 32(37):4839–4842.
Metcalf, R. L., R. A. Metcalf (1993) "Insects that Affect the Health of Humans" In: *Destructive and useful insects: their habits and control* McGraw-Hill, Inc., Frank J. Kotowski, Jr., ed., pages 21.42–21.47.
Scott, Jeffrey G. (1998) "Toxicity of Spinosad to Susceptible and Resistant Strains of House Flies, *Musca domestica*" *Pestic. Sci.* 54:131–133.

I claim:

1. A device for controlling houseflies, said device comprising:
   (a) an absorbent material, comprising a lower portion and an upper portion, wherein said lower portion of said absorbent material is substantially covered by a non-absorbent material, and wherein said upper portion of said absorbent material is absorbed with an insecticidal composition, wherein said insecticidal composition comprises:
      (i) spinosad; and
      (ii) a foodstuff that houseflies will feed on, said foodstuff comprising sugar, milk and eggs; and
      (iii) an attractant, said attractant comprising cornmeal and yeast;
   wherein said insecticidal composition comprises from about 0.01% to about 1% of said spinosad based on dry weight of said insecticidal composition; and
   (b) a reservoir capable of containing a solution and adapted for releasably holding said lower end of said absorbent material in said solution.

2. The device according to claim 1, wherein the spinosad of said insecticidal composition comprises about 85% spinosyn A and about 15% spinosyn D.

3. The device according to claim 2, wherein said spinosad is provided in the form of a spinosad waste broth.

4. The device according to claim 3, wherein said insecticidal composition comprises about 60% spinosad waste broth.

5. The device according to claim 1, wherein the total dry weight of said absorbed insecticidal composition is from about 1 to about 3 grams.

6. The device according to claim 1, wherein said absorbent material is capable of transporting said solution contained in said reservoir from said absorbent material lower portion to said absorbent material upper portion.

7. The device according to claim 1, wherein said absorbent material is selected from the group consisting of cotton, felt, muslin, sponge, blotting paper, and cloth.

8. The device according to claim 1, wherein said solution contained within said reservoir comprises water.

9. The device according to claim 1, wherein said insecticidal composition comprises about 0.1% spinosad.

10. The device according to claim 1, wherein said insecticidal composition comprises about 60% of said foodstuff.

11. The device according to claim 1, wherein said insecticidal composition comprises from about 30% to about 40% of said cornmeal.

12. The device according to claim 1, wherein said insecticidal composition comprises from about 2% to about 4% of said yeast.

13. The device according to claim 1, wherein said insecticidal composition further comprises water.

14. The device according to claim 13, wherein said insecticidal composition is a slurry in a ratio of about one gram of dry material to about one milliliter of water.

15. The device according to claim 13, wherein said insecticidal composition is a slurry in a ratio of about one gram of dry material to about 0.5 milliliter of water.

16. The device according to claim 1, wherein said device further comprises a means for attracting insects.

17. The device according to claim 16, wherein said means for attracting insects comprises a pheromone.

18. The device according to claim 17, wherein said pheromone comprises cis-9-tricosene.

19. The device according to claim 1, wherein said device further comprises an antimicrobial agent.

20. The device according-to claim 19, wherein said antimicrobial agent comprises an antifungal agent.

21. A method for controlling houseflies, said method comprising providing to said houseflies an insecticidal composition comprising:

(i) spinosad; and (ii) a foodstuff that houseflies will feed on, said foodstuff comprising sugar, milk, and eggs; and (iii) an attractant, said attractant comprising cornmeal and yeast;

wherein said insecticidal composition comprises from about 0.01% to about 1% of said spinosad based on dry weight of said insecticidal composition;

and absorbing said insecticidal composition onto said upper portion of said absorbent material of said device of claim 1.

22. The method according to claim 21, further comprising placing a solution in said reservoir of said device and permitting said absorbent material to transport said solution from said absorbent material lower portion to said absorbent material upper portion.

23. The method according to claim 21, wherein said spinosad comprises about 85% spinosyn A and about 15% spinosyn D.

* * * * *

UNITED STATES PATENT AND TRADEMARK OFFICE
CERTIFICATE OF CORRECTION

PATENT NO. : 6,821,526 B1
DATED : November 23, 2004
INVENTOR(S) : Xinpei Huang

It is certified that error appears in the above-identified patent and that said Letters Patent is hereby corrected as shown below:

Column 6,
Line 36, "highly effective, The" should read -- highly effective. The --.

Column 12,
Line 9, "according-to" should read -- according to --.

Signed and Sealed this

Third Day of May, 2005

JON W. DUDAS
*Director of the United States Patent and Trademark Office*